US006458367B1

(12) United States Patent
Verschoor et al.

(10) Patent No.: US 6,458,367 B1
(45) Date of Patent: Oct. 1, 2002

(54) METHOD FOR DETECTING THE PRESENCE OF A MYCOBACTERIUM SPECIES AND A KIT AND ANTIBODIES FOR USE THEREIN

(75) Inventors: Jan Adrianus Verschoor, Pretoria (ZA); Sandra Noel Bye, Hilton (ZA)

(73) Assignee: Adcock Ingram Limited

( * ) Notice: Subject to any disclaimer, the term of this patent is extended or adjusted under 35 U.S.C. 154(b) by 0 days.

(21) Appl. No.: 09/304,893

(22) Filed: May 4, 1999

Related U.S. Application Data

(62) Division of application No. 08/722,055, filed as application No. PCT/GB95/00856 on Apr. 13, 1995, now Pat. No. 6,124,105.

(30) Foreign Application Priority Data

Apr. 14, 1994 (ZA) .............................................. 94/2575
Feb. 22, 1995 (ZA) .............................................. 95/1464

(51) Int. Cl.[7] ........................ A61K 39/04; A61K 39/38; A61K 39/385; A61K 39/02

(52) U.S. Cl. ................................ 424/248.1; 424/184.1; 424/193.1; 424/194.1; 424/197.11; 424/234.1; 424/278.1

(58) Field of Search ........................... 424/184.1, 248.1, 424/234.1, 278.1, 193.1, 194.1, 197.11

(56) References Cited

FOREIGN PATENT DOCUMENTS

| | | |
|---|---|---|
| EP | 0407605 | 7/1990 |
| WO | 8505034 | 11/1985 |
| WO | 9500163 | 1/1995 |
| WO | 9503418 | 5/1995 |
| WO | 9612190 | 4/1996 |

OTHER PUBLICATIONS

Hinrikson et al "Mycobacterial Mycolic Acids", Medical Microbiology Letters, vol. 3, pp. 49–57, 1994.*

Merck Index, $10^{th}$ edition, 6173 (Mycolic Acids).

Hamid et al., "A Simple Chemical Test . . . ", Journal of General Microbiology (1993), 139, 2203–2213.

Young, D., "Identification of Mycobacterium . . . ", Journal of General Microbiology (1980), 121, p. 249–253.

Butler et al., "High–Performance Liquid . . . ", Journal of Clinical Microbiology, Sep. 1990, p. 2094–.

Minnikin et al., "Comparative Studies of Antigenic Glycolipids of Mycobateria Related to Leprosy Bacillus", ACTA Leprol. 1(suppl. 1): 51–54, 1989.

Bultler et al., "Identification of Mycobacteria . . . ", Journal of Clinical Microbiology, Nov. 1991, p. 2468–2472.

Mason et al., "The Use of Monoclonal Antibodies . . . ", Tuberculi & Lung Disease, pp. 195–199.

Wiker et al., "A localization index for distinction . . . ". Journal of General Microbiology (1991), 137, 875–884.

Bothanley, G.H., "Serological diagnosis of tuberculosis", Eur. Respir J. 1995, 8, Suppl, 20:676s–688s.

Daniel et al., "The Serodiagnosis of Tuberculosis and Other Mycobacterial Diseases by Ensyme–linked Immunosorbent Assay", Am. Rev, Respir. Dis.1987, 135:1137–1151.

He, H., etal, "Rapd serodiagnosis of human nycobacteriosis by ELISA . . . ", FEMS Microbio Immunology (1991) 76:201–204.

Kato, M., "Antibody Formation to Treholose . . . ", Infection and Immunity, Feb. 1972, pp. 203–212.

Kato, M., "Immunochemical Properties of Anti–Cord Factor Antibody", Infection and Immunity, Jan. 1973, pp. 9–13.

Kolk et al., "Producíont and Characterization of Monoclonal Antibodies . . . Arend", Infection and Immunity, Aug. 1989, pp. 2514–2521.

Maekura, R., "Clinical Evaluation of rapid Serodiagnosis of Pulmonary Tuberculosis by ELISA with Cord Factor", Am. Rev. Respir Dis (1993) vol. 148, pp. 987–1001.

Fadda et al., "Serodiagnosis and Follow Up of Patients with Pulmoney Tuberculosis by Enzyme–Linked . . . ", Eur. J. Epiderio, 0392–2990, Jan. 1992, pp. 81–87.

* cited by examiner

*Primary Examiner*—Rodney P Swartz
(74) *Attorney, Agent, or Firm*—Ladas & Parry

(57) ABSTRACT

The invention relates to a diagnostic test for the detection and identification of Mycobacterium species in biological specimens of human and animal origin. The test is based on the immunological detection of one or more antigens originating from Mycobacterium. To enable the detection of an antibody-antigen reaction, the antibodies specific for these antigens can be labelled with an enzyme or fluorescent dye or attached to latex particles or any other suitable label. The diagnostic test may be in a form of ELISA and may or may not require concentration of the Mycobacterium antigens prior to the actual test. The invention comprises: the selection and procurement of a suitable mycobacterial species and strain, the isolation and purification of the antigens, preparation of the necessary conjugates for the immunization of the experimental animals using various carrier molecules, the development of an assay for monitoring the antibody production, caracterization of the antibodies specific for the Mycobacterium antigen/antigens and the development of a diagnostic assay/kit.

11 Claims, 5 Drawing Sheets

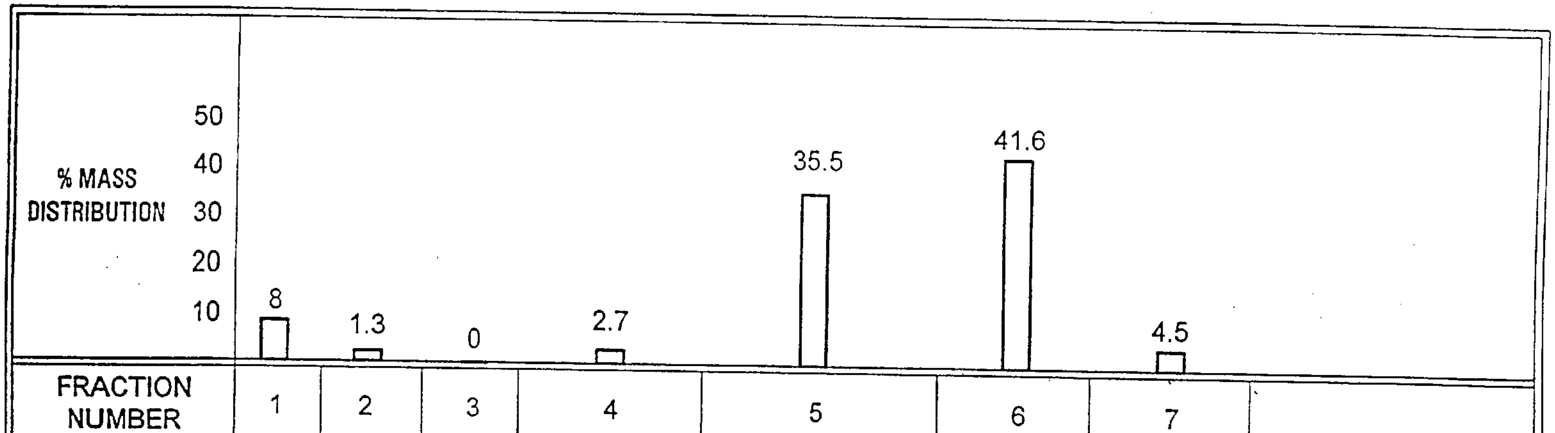

| FRACTION NUMBER | 1 | 2 | 3 | 4 | 5 | 6 | 7 |
|---|---|---|---|---|---|---|---|
| TUBE NUMBER | 0 1 | 2 3 4 | 5 6 7 | 8 9 10 11 | 12 13 14 15 16 17 18 19 | 20 21 22 | 23 24 |
| YIELD ( mg ) | 3.0 | 0.5 | 0 | 1.0 | 13.3 | 15.6 | 1.7 |
| DISTRIBUTION CONSTANT $K_d$*) | 0.08 | | – | 1.26 | | 5.5 | 16.3 |
| EMULSIFICATION PATTERN | LOWER PHASE | | NONE | LOWER PHASE | UPPER PHASE | NONE | NONE |
| PHYSICAL NATURE | MYCOLIC ACIDS | | NONE | SOAP(SAPONIFIED FATTY ACIDS) | | CRYSTALLINE SUGAR | NON-CRYSTALLINE ORGANIC COMPOUND |
| SOLUBLE IN: | CHLOROFORM | | – | CHLOROFORM: METHANOL ( 3 : 7 V/V ) | | 50% METHANOL-WATER | 50% METHANOL-WATER |

TOTAL: 35.1

$$*)\ K_d = \frac{r_{max} + 1}{n - r_{max}}$$

FIG. 4

METHOD FOR DETECTING THE PRESENCE OF A MYCOBACTERIUM SPECIES AND A KIT AND ANTIBODIES FOR USE THEREIN

This is a divisional of application Ser. No. 08/722,055, filed Feb. 11, 1997 (now U.S. Pat. No. 6,124,105), which is a 371 of PCT/GB95/00856, filed Apr. 13, 1995.

BACKGROUND OF THE INVENTION

This invention relates to a method, based on an immunological approach, for detecting the presence of a Mycobacterium species and a kit and antibodies for use therein.

The various known species of Mycobacterium are known to cause a number of infectious diseases in humans and animals. One such Mycobacterium species, *Mycobacterium tuberculosis*, causes tuberculosis in humans.

Tuberculosis is considered to be the major communicable disease throughout most of the world. Despite great advances in medical science and a range of effective drugs, which for some time created the impression that the disease had been conquered, and despite organised international efforts, tuberculosis remains a world health problem of staggering proportions. More than 8 million new cases world-wide and more than 3 million deaths were reported in the year 1990 alone (Snider, 1994). Predictions made by the World Health Organisation indicate that by the year 2000 the annual figures will grow to 10.2 million new cases and 3.5 million deaths, with Asia and Sub-Saharan Africa being the most affected continents (Dolin, Raviglione and Koch, 1994). The global distribution of the estimated number of tuberculosis cases for the current decade and the estimated number of deaths for the same period is presented in Dolin, Raviglione and Koch, 1994.

The close association documented between tuberculosis and AIDS as well as the frequently concomitant presence of both these diseases add gravity to the situation (Torres et al., 1990; De Cock, 1994; Cantwell and Binkin, 1994; Murray, 1994). The emergence of multiple-drug resistance among the strans of Mycobacterium tuberculosis and other atypical mycobacteria has introduced an additional dimension to this gigantic problem (Blumberg, Miller and Koornhof, 1994; Morse, 1994).

The accurate and timely detection of tuberculosis and related mycobacterial diseases is one of the important requirements to develop a more successful global strategy to combat these diseases.

Traditional laboratory detection methods have major disadvantages of either not being capable of distinguishing between live and dead bacilli (the quick and simple Ziehl-Neelsen staining) or, if these methods confirm the presence of the live bacilli (direct cultivation), a number of weeks is required before the laboratory tests are completed. This, in turn, may delay the commencement of treatment and may lead to further spread of the disease.

The more recent approaches are based either on the detection of patients' response to the infection by methods such as serological tests, lymphocyte proliferative responses to mycobacterial antigens or by determining the level of adenosine deaminase, or on the detection of mycobacterial antigens and constituents using immunoassays such as ELISAs, gas and liquid chromatography or mass spectrophotometry. More modern, molecular approaches include polymerase chain reaction (PCR), DNA probes or DNA fingerprinting (Musial et al., 1988; Godfrey-Faussett, 1994).

Mason et al, 1993 (Tubercle and Lung Disease) describe a method of identification and characterization of mycobacterial species by using monoclonal antibodies inter alia directed to mycobacterial lipoarabinomannan and unspecified glycolipids.

Wiker et al, 1991 (Journal of General Microbiology) describe a method for characterizing and identifying mycobacterial species grown in culture by detecting characteristic protein antigens of mycobacteria.

Hamid et al, 1993 (Journal of General Biology) describe a text to distinguish Mycobacteria from other bacteria by precipitating mycolic acids and performing a TLC analysis on them.

Young 1980 (Journal of General Biology) describe a method for extracting and analyzing mycolic acids from mycobacteria by TLC and shows a difference in the mycolic acid profile between *Mycobacterium leprae* and other bacteria in leprosy biopsies.

European Patent Application No 0407605 details a method of detecting antibodies in patient sera to bacteria from the species Nocardia by detecting antibodies raised to nocardial mycolic acids.

However, none of the methods listed above fulfills all the requirements for a quick, simple and reliable test capable of distinguishing between live and dead mycobacteria cells.

SUMMARY OF THE INVENTION

According to the invention there is provided a diagnostic assay for detecting and identifying a Mycobacterium species in a biological sample of an animal by immunologically detecting at least one intra-cellular mycobacterial antigen of the species in. the sample.

"Intra-cellular mycobacterial antigen" is defined herein to be a non-surface antigen or a metabolic product of the Mycobacterium species.

The intra-cellular mycobacterial antigen is preferably detected by exposing the biological sample to an antibody or antibodies specific for the intra-cellular mycobacterial antigen.

The assay preferably comprises the step of lysing at least some of the mycobacterial cells present in the sample to release at least some of the antigen present in their cell walls prior to contacting the sample with antibody.

The assay preferably also comprises the steps of treating the biological sample to release the mycobacterial cells from any organic debris in which they may be embedded and decontaminating the biological sample to eliminate unwanted microorganisms present in it prior to lysing the mycobacterial cells.

The intra-cellular mycobacterial antigen is preferably a mixture of mycolic acids present in the cell wall of the Mycobacterium species, each having the following general structure:

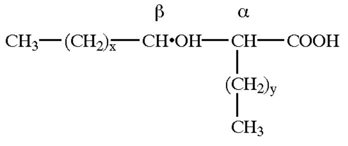

The biological sample is preferably sputum, blood, cerebro-spinal fluid, stool, urine, gastric lavage, saliva, tissue, a laryngeal swab or an exudate from a skin lesion.

The assay preferably also comprises the step of concentrating the mycolic acids in the sample by an immobilized antibody affinity procedure prior to contacting them with a labelled antibody. The concentration step is preferably carried out using an immuno-affinity column.

According to another aspect of the invention a method for group separation and subsequent purification of mycobacterial mycolic acids having the general structure set out above from a mixture of extracted mycobacterial mycolic acids and contaminants comprises the steps of:

dissolving the mixture of mycolic acids and contaminants in a bi-phasic solvent; and subjecting the mixture to liquid-liquid phase separation.

Preferably, the purified mycolic acids are not subsequently chemically derivatized.

The bi-phasic solvent system preferably comprises chloroform, methanol and water.

Preferably, the bi-phasic solvent system comprises an upper phase and a lower phase.

The method preferably also comprises the steps of mixing and equilibrating the upper and lower phases.

Preferably, the composition of the upper phase is 12–18% chloroform, 45–55% methanol and 20–40% water. More preferably, the composition of the upper phase is 15% chloroform, 52% methanol and 33% water.

Preferably, the composition of the lower phase is 50–80% chloroform, 5–40% methanol and 2–8% water. More preferably, the composition of the lower phase is 68% chloroform, 27% methanol and 5% water.

The purification is preferably performed using a countercurrent apparatus or any other liquid-liquid extractor.

According to another aspect of the invention a purified mycolic acid having the following general structure:

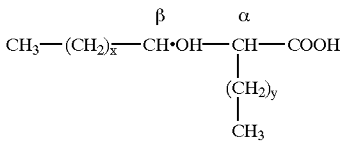

group separated and purified is provided.

According to another aspect of the invention an antibody to an intra-cellular mycobacterial antigen is provided.

The antibody may be monoclonal or polyclonal and is preferably of animal origin.

The antibody is preferably an isolated polyclonal antibody raised to a mycolic acid purified by the above method.

According to another aspect of the invention a mycobacterial intra-cellular antigen/carrier conjugate is provided.

The intra-cellular antigen is preferably a mycolic acid and it is preferably adsorbed onto the carrier.

The carrier may be a protein such as bovine serum albumin, gelatin or keyhole limpets hemocyanin.

According to yet another aspect of the invention a kit for detecting the presence of a Mycobacterium species in a biological sample comprises:

an antibody raised to a mycolic acid purified by the above method and detectably labelled.

The kit may also comprise an amount of a mycobacterial mycolic acid/carrier conjugate and optionally also an immobilized antibody.

BRIEF DESCRIPTION OF THE DRAWING

FIG. 4 shows the mass distribution pattern of components in the countercurrent purified material extracted from *M. tuberculosis*, based on HPLC analysis.

DETAILED DESCRIPTION OF THE INVENTION

Figure 1:
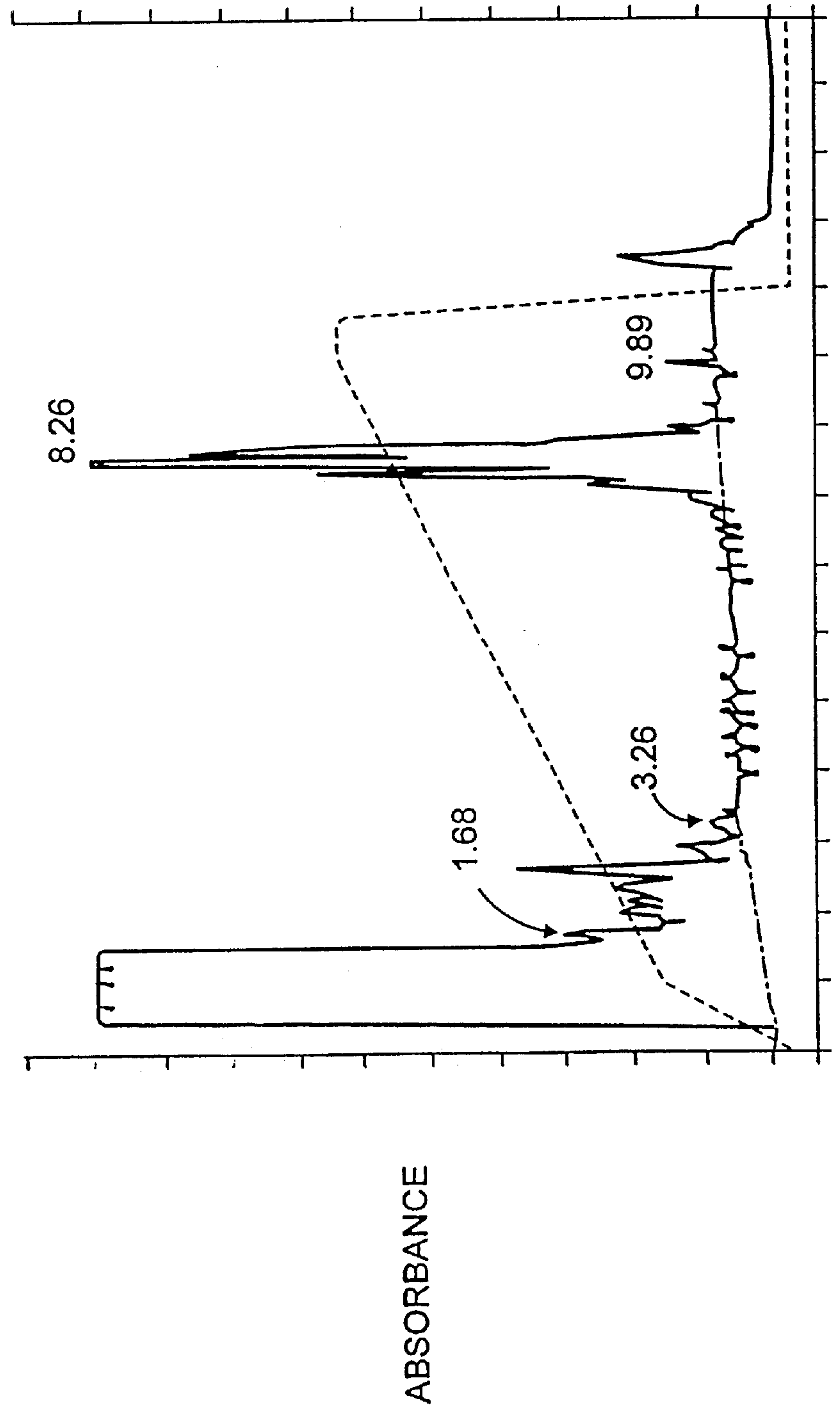
FIG. 1 shows the HPLC profile of a crude mycolic acids extract from *M. tuberculosis;*

The aim of the present invention is to develop a diagnostic test for the confirmation of the presence of Mycobacteria in biological specimens of human or animal origin, such as sputum, cerebro-spinal fluid, blood, urine, stools or tissue samples, gastric lavage, saliva, laryngeal swab or an exudate from a skin lesion.

The test is based on the immunological detection of one or more cellular antigens/mycolic acids originating from Mycobacteria. The test may be based on the use of antibodies labelled with an enzyme, fluorescent dye, latex particles or any other suitable label.

Mycolic acids are high molecular weight α-hydroxy fatty acids which have moderately long aliphatic chains at the α-position.

As it is known that each species of the genus Mycobacterium is characterized by a unique type of mycolic acids (Butler, Jost and Kilburn, 1991; Butler and Kilburn, 1988), it should be possible to distinguish between various members of the genus using specific antibodies supplied in the assay.

EXAMPLE 1

The investigations which form the basis of the invention, whereby a method is provided for the detection and identification of a Mycobacterium species in a biological specimen comprised the following stages:

Stage 1 Procurement of the Mycobacterium strains. The cultures were purchased from the American Type Culture Collection (ATCC);

Stage 2 Isolation of mycolic acids from Mycobacterium cultures, identification of mycolic acids by HPLC analysis and their purification;

Stage 3 Preparation of mycolic acids conjugates using BSA, KLH and gelatin as carrier molecules;

Stage 4 Immunization of the experimental animals and production of antibodies specific for mycolic acids. Characterization of antibodies;

Stage 5 Proposed development of a diagnostic test/assay (making antigen-antibody reactions detectable);

Stage 6 To be followed by evaluation of the diagnostic test/assay: confirmation of the assay's specificity and sensitivity, field tests, comparison with the existing tests/assays;

The materials, (including the experimental animals). methods and results used during the investigations are described below.

MATERIALS

As used herein, the following trademarks identify products having the indicated general descriptions:

WISP—a small glass vial in which samples for HPLC analysis are prepared.

TEFLON—polytetrafluoroethylene resin.

ADJUPRIME—a carbohydrate polymer used as an adjuvant for enhancement of immune response.

EPPENDORFF—microcentrifuge polyethylene tubes.

PARAFILM—a rubber composition.

Culture

*Mycobacterium tuberculosis* H37Rv ATCC 27294—a virulent strain, originally isolated from an infected human lung, was used in the experiments.

The culture was purchased in lyophilized form from the American Type Culture Collection (ATCC), Maryland, USA.

Media

The following media were used for the cultivation of *M. tuberculosis:*

Liquid medium: Dubos broth

Solid media: Löwenstein-Jensen (LJ) medium
Middlebrook 7H-10 medium

A detailed composition of the ingredients necessary for the preparation of these media as well as the conditions recommended for their sterilization, are given in the Laboratory Manual of Tuberculosis Methods, Tuberculosis Research Institute of the SA Medical Research Council (1980, Chapter 6, pp 83–105; Second Edition, revised by E E Nel, H H Kleeberg and E M S Gatner).

The media were prepared by the Department of Medical Microbiology at the Institute for Pathology of the University of Pretoria.

Reagents

The following reagents were used for the saponification, extraction, derivization and High-Performance Liquid Chromatography (HPLC) analysis of mycolic acids:

Reagent A: 25% potassium hydroxide (Analytical Grade) dissolved in methanol-water (1:1); 62.5 g potassium hydroxide was dissolved in 125 ml water and 125 ml methanol (BDH, HPLC Grade) was added.

Reagent B: Concentrated hydrochloric acid (BDH, Analytical Grade) diluted 1:1 with water.

Reagent C: 2% potassium bicarbonate (BDH, Analytical Grade) dissolved in methanol-water (1:1): 10 g potassium bicarbonate was dissolved in 250 ml water and 250 ml methanol was added.

Reagent D: para-bromophenacylbromide in Crown Ether (Pierce Chemical Co, Cat. No 48891) was dispensed in 500 μl quantities into small amber-coloured screw cap vials with Teflon. (this is a registered trade mark) coated septa. The caps were tightened and the vials were wrapped with Parafilm (this is a registered trade mark). Reagent D was stored at 4° C.

Reagent E: Reagent E was prepared by mixing reagent B 1:1 with methanol.

HPLC Standard:

High Molecular Weight Internal Standard (C-100) from Ribi ImmunoChem Research Company, Cat No R-50. The standard, 1 mg, was suspended in 2.0 ml methylene chloride (BDH, HPLC Grade), aliquots of 350 μl were dispensed into small screw-cap vials with TEFLON (this is a registered trade mark) coated septa. The vials were wrapped with PARAFILM (this is a registered trade mark) and stored at 4° C. To limit evaporation of methylene chloride, the HPLC standard aliquots were maintained on ice during handling.

Chloroform (Associated Chemical Enterprises, Chemically Pure Grade)

Methylene chloride (BDH, HPLC-Grade)

Reagents A, B, C and E were prepared fresh prior to experiments, taking all the necessary safety precautions.

Double-stilled deionized water was used for the preparation of the reagents.

The following reagents were used in the purification of the extracted mycolic acids:

Chloroform (Saarchem, Analytical grade) Methanol (Merck, Chemically pure)

The following reagents were used for the immunization of the experimental animals:

Bovine Serum Albumin (BSA)—Sigma Lot 11H1040

Mycolic acids-BSA conjugates

Keyhole Limpets Haemocyanin—KLH Sigma Immuno Chemicals

Mycolic acids-KLH conjugates

Freund's Incomplete Adjuvant (FIA)

ADJUPRIME (this is a registered trade mark) Immune Modulator (Pierce Chemical Company, Cat No 77138)

Sterile saline—0.85% m/v solution of sodium chloride in double distilled water.

The following reagents were used in the development of ELISA for the detection of antibodies specific for mycolic acids:

Bovine Serum Albumin (BSA)—Sigma Lot 11H1040

Gelatin (Serva, Lot 22151, Reinst-Research Grade)

Gelatin-MA conjugate

PBS—Phosphate buffered saline (pH 7.4), comprising:
- Sodium chloride (Unilab, Chemically Pure Grade, Lot 28159)
- Sodium hydrogen phosphate dodecahydrate (Merck, Chemically Pure Grade, Lot 7468715)
- Potassium chloride (Merck, Chemically Pure Grade, Lot 6420150)
- Potassium dihydrogen phosphate (Merck, Chemically Pure Grade, Lot 6332422)

Citrate buffer (pH 4.5) comprising:

0.1 M Citric acid (Merck, Lot 775A)

0.1 M Tri-sodium citrate (Merck, Lot 8533833)

Casein (Merck, Lot 0100 336 V279342)

0-Phenylenediamine (dihydrochloride) (Sigma, Lot 59F-5021)

Methanol (Saarchem, Analytical Grade, Batch 31260) Goat anti-mouse monoclonal antibody-peroxidase conjugate (Cappel, Lot 37081)

Substrate: 8 mg urea hydrogen peroxidase 10 mg o-Phenylenediamine in 10 ml 0.1 M Citrate buffer.

Serum samples originating from five immunized and three control mice were used in this experiment.

Experimental Animals

Six weeks old, female Balb-C mice were used in the immunization experiments. The mice were bred by the Animal Centre at the South African Institute for Medical Research in Johannesburg.

ELISA plates

Nunc Immunoplates (Maxisorp) plates were used for ELISA tests.

Countercurrent Separation Apparatus

A countercurrent apparatus produced by H O POST, Instrument Company Inc., Middle Village, N.Y. was used during the investigations.

METHODS

The following methods were used in the experimental work:

Cultivation of the Bacterial Strain

The bacteria were cultivated at 37° C. using:

Dubos broth

Löwenstein-Jensen medium (slants), and

Middlebrook 7H-10 agar medium (slants).

Preparation of Mycolic Acids from Bacterial Samples

The preparation of bacterial samples comprised three steps:

harvesting of the Mycobacteria cells;

saponification and extraction of mycolic acids.

The saponification, extraction and derivatization of mycolic acids were carried out as described by Butler, Jost and Kilburn (1991), with minor modifications and are described under the relevant heading.

Glassware used for the extraction, derivatization and HPLC analyses of mycolic acids was washed in 2% (v/v) Contrad (Merck), rinsed in water, followed by rinsing in chloroform, water, technical Grade ethanol, water and finally rinsed in double distilled deionized water. The washed glassware was dried in a warm air oven.

Harvesting was done by scraping the bacterial growth from the surface of media slants (using sterile plastic loops). Homogenous bacterial suspensions were prepared in reagent A, by shaking or vortexing the harvested cells with sterile glass beads.

Saponification of the Mycobacteria in Reagent A was carried out in an autoclave at 121° C., for one hour.

Extraction of mycolic acids comprised the following:

The samples were allowed to cool and 1.5 ml Reagent B was introduced to each sample. After vortexing, the pH of each sample was checked and if necessary, adjusted to pH 1 with reagent B.

Subsequently, 2.0 ml chloroform was added to each sample and vortexed for 30 seconds. The layers were allowed to separate. The bottom layers were removed with Pasteur pipettes, transferred to WISP vials and evaporated to dryness at 85° C. in a heat block-evaporator under a stream of nitrogen. To neutralize traces of acid carried over, 100 μl of reagent C was added to each sample and the fluid evaporated to dryness at 85° C. in a heat block-evaporator under a stream of nitrogen.

Derivatization of Mycolic Acids for HPLC Analysis

Extracted mycolic acids were derivatized as follows:

To each cooled sample 1.0 ml chloroform was introduced, followed by the addition of 50 μl of Reagent D. The capped samples were vortexed for 30 seconds and heated for 20 minutes at 85° C. in a heat block-evaporator. Subsequently, the samples were cooled and 1.0 ml of Reagent E added. The samples were vortexed for 30 seconds and the layers allowed to separate. The bottom layers were removed with Pasteur pipettes and transferred to WISP-vials. The vials were placed in a heat block-evaporator and their contents evaporated to dryness at 85° C. using a stream of nitrogen.

The residues were resuspended in 0.212 g (which corresponds to 160 μl) methylene chloride, capped and vortexed. Each reconstituted sample, into which 5 μl HPLC internal standard was introduced, was filtered through a 0.45 μm membrane filter into an amber-coloured WISP-vial. The recapped vials were stored at 4° C. until ready for HPLC analysis.

HPLC Analysis and Quantification of Mycolic Acids

For the HPLC analysis 25 μl from each sample (maintained on ice during handling), was analyzed. Control samples, i.e, 25 μl of filtered methylene chloride, were run prior to each set of samples analyzed. If a large number of samples was analyzed, in order to validate the reliability of the HPLC apparatus, control samples were run after every three or four test samples.

The reverse-phase HPLC analyses were carried out using a Beckman System Gold High Performance Liquid Chromatography apparatus consisting of:

Pumps (Beckman 110 B Solvent Delivery Module);

Detector (Programmable detector module 166 or 168);

Column (Nova-Pak C18 4 μm 3.9×150 mm) and an end connector set for steel cartridge columns.

Running conditions were:

Mobile phase:

Solvent A: HPLC Grade Methanol

Solvent B: HPLC Grade Methylene chloride

Flow Rate: 2.5 ml/min

Column temperature: 30° C.

The detector was set at 260 nm.

The HPLC gradient initially comprised 98% (v/v) methanol (Solvent A) and 2% (v/v) methylene chloride (Solvent B). The gradient was increased linearly to 80% A and 20% B at one minute; 35% A and 65% B at ten minutes, held for 30 seconds and then decreased over 30 sec back to 98% A and 2% B. This ratio was maintained for 4 minutes to allow for stabilization of the system prior to injection of the next sample.

Mathematical quantification of mycolic acids was carried out by comparing the combined peak areas of the tested samples to the peak area of the introduced quantity of the High Molecular Weight Internal HPLC Standard.

Purification of Mycolic Acids and Group Separation of other Fatty Acids

A countercurrent distribution train comprising 25 tubes, numbered 0–24, was used in the experiment. Into a buffer reservoir approximately 900 ml of the upper phase was introduced.

Into tube number 0, a sample of the crude cellular extract of *M. tuberculosis* obtained from a large-scale extraction experiment (30–150 mg), dissolved in 10 ml of the lower phase and 10 ml of the upper phase was introduced. Into the remaining 24 tubes aliquots of 10 ml of the lower phase were introduced. Upper phase, in volumes of 10 ml per cycle, was automatically dispensed into tube number 0, repeatedly over 25 cycles resulting in approximately 16 hour operation. Thus, twenty five countercurrent cycles were performed, with each cycle consisting of 20 mixing pendula and 40 minutes phase separation time.

With each transfer, any solute originating from the sample and present in the upper phase is carried into the succeeding tube. After the completion of twenty five transfers, the separated solute fractions should be distributed along the train of 25 tubes.

To establish the distribution of fatty acids among the twenty five tubes, the emulsification patterns in upper and lower phases were observed within the tube train and fractions were determined accordingly.

The countercurrent-separated material was then withdrawn from the tubes using a 50 ml glass syringe, with a TEFLON tubing attached. The material was pooled into seven fractions, dried individually under vacuum in a Buchi evaporator at 70° C., the dried material redissolved in either chloroform, methanol or water (in approximately 5 ml), transferred into amber WISP-vials and stored at 4° C. until required.

Yield of the Mycolic Acids Purified by Countercurrent Separation

In order to calculate the approximate yield of purification/separation, the weighed amount of the mycolic acids present in the samples obtained after the countercurrent separation/purification was compared to the amount of these compounds present in the crude cellular extract introduced into the countercurrent apparatus, calculated from the relative peak areas of the mycolic acids peak cluster and that from the peak area of the standard in the HPLC chromatogram of the crude cellular extract.

Countercurrent Purification of Mycolic Acids

The material extracted from *M. tuberculosis*, according to the method proposed by Butler, Jost and Kilburn (1991) for the isolation of mycolic acids, was found to contain less than 10% mycolic acids (Table 1). In order to render mycolic acids immunogenic, it is necessary to attach the purified material to carrier molecules such as bovine serum albumin. An important requirement of this procedure is the solubility ratios of mycolic acid in a suitable solvent.

Countercurrent purification of crude mycolic acids extract from *M. tuberculosis* H37Rv ATCC 27294 using the phase system described above, was performed over 25 cycles.

Upon mixing the final phases in the tube train and allowing them to settle for a few minutes, an emulsification pattern could be observed which indicated quite accurately how the material was distributed over the tube train.

Figure 2:
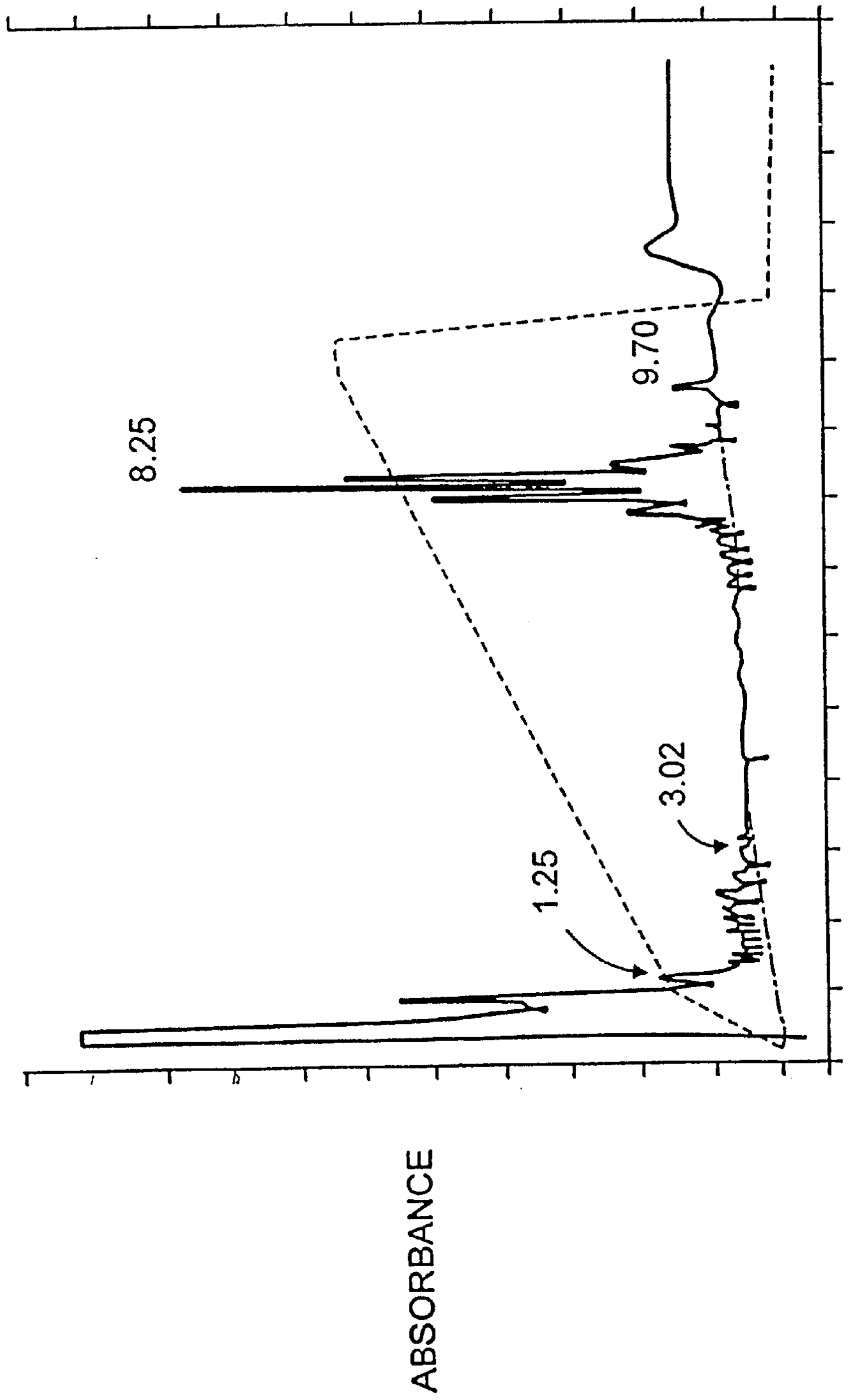
FIG. 2 shows the HPLC profile of fraction 1 of the countercurrent purified mycolic acids extract from *M. tuberculosis;*
Figure 3:
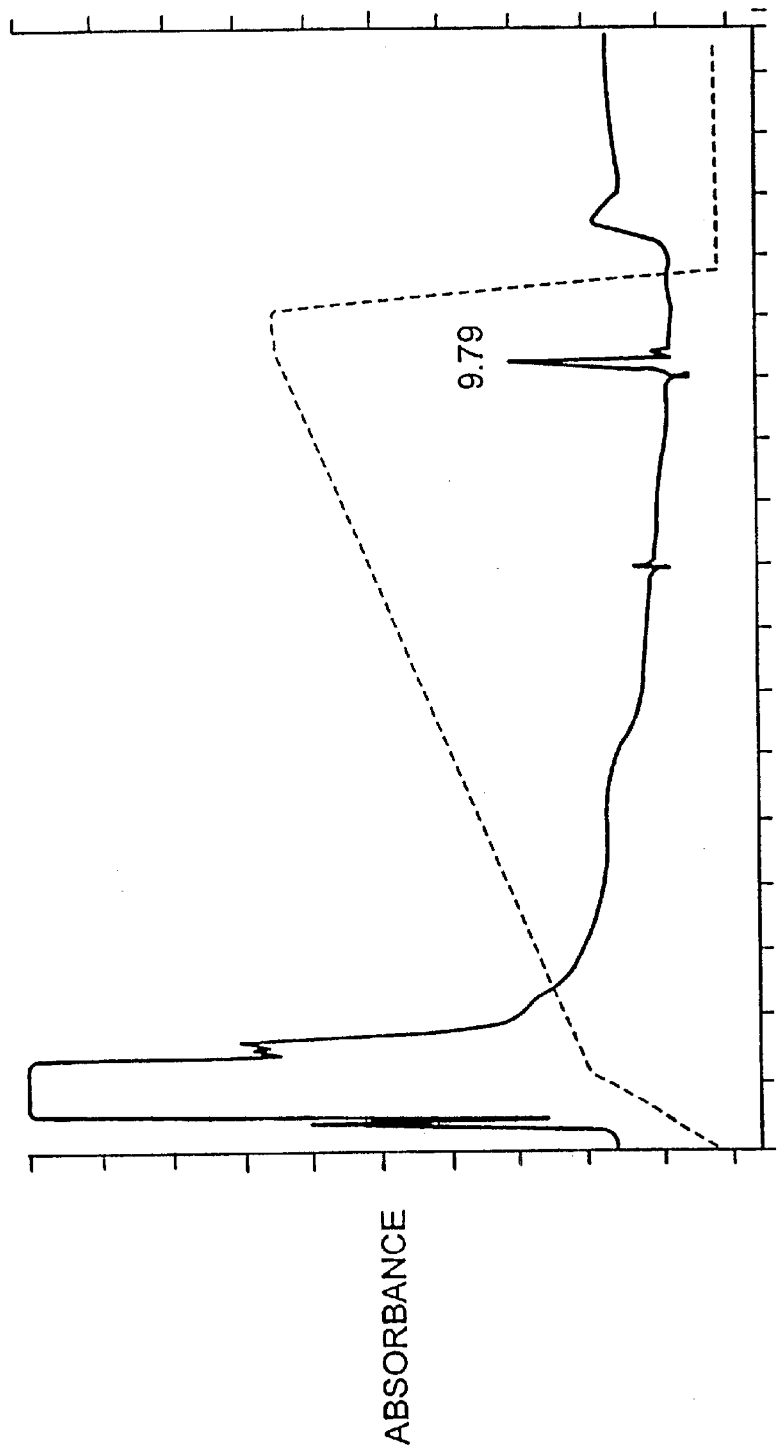
FIG. 3 shows the HPLC profile of fraction 4 of the countercurrent purified mycolic acids extract from *M. tuberculosis;*

Fractions 1, 2, 3, 4 and 5 were analyzed by HPLC, which revealed the mycolic acid nature of peaks 1 and 2, and the short chain fatty acid nature of peaks 4 and 5 (FIGS. 1–3).

The HPLC profiles of the crude cellular extract, fraction 1 and fraction 4 are presented in FIGS. 1–3.

Fractions 6 and 7 could not be analyzed by HPLC due to the fact that they were not soluble in chloroform.

The mass distribution pattern (FIG. 4) indicates that base-line separation of mycolic acids from its more polar contaminants was achieved, while the yield of 8% correlated with theoretical yield of mycolic acids from the crude extract within the limits of experimental error.

As becomes evident from FIGS. 1–3, fraction 1 indeed contained the purified mycolic acids.

Preparation of Mycolic acids-BSA Conjugate

A solution of BSA containing 5 mg in 500 $\mu l$ of a 0,1 N $NaHCO_3$ (pH 8.3) was prepared. A sample of countercurrent-purified mycolic acid (4.5 mg) was dissolved in 450 $\mu l$ chloroform. The BSA solution was added slowly to an aliquot of 200 $\mu l$ of the mycolic acids solution over a period of 1 min 20 sec, at room temperature. During this process the mixture was being vortexed. After an additional vortexing for 30 sec, the sample was placed on ice for 15 minutes. Ice-cold acetone (2 ml) was then introduced over a period of two minutes, while the sample was maintained on ice. The mixture was left to stand for half an hour.

After withdrawing a quarter of the solution into another vial for HPLC analysis (0.5 mg), the sample was centrifuged with three short 10 sec centrifugation pulses and the pellet rinsed twice with acetone. The pellet was then transferred back into the WISP vial, allowed to air-dry and maintained at 4° C. overnight under foil. The sample withdrawn for HPLC analysis was dried on the heat block.

The addition of the adjuvant was carried out as follows:

A sample of ADJUPRIME (this is a registered trade mark) Immune Modulator (10 mg) was ground with a glass rod and a sample of mycolic acids-BSA conjugate (1 mg), dried on the heat block was added. The powders were ground together to obtain a homogenous powder of which 1 mg was weighed off and dissolved in 1 ml sterile saline. The remaining ADJUPRIME (this is a registered trade mark) BSA-mycolic acids mixture was sealed under a vacuum, covered in foil and stored at 4° C.

The saline solution was sonified using a Branson Sonifier—Cell disruptor B-30 for ten 10 sec-pulse cycles with 10 sec breaks, followed by one 30 sec pulse cycle, which resulted in uniform dispersion of the particles. During the sonification, the sample was maintained on ice. According to the instruction attached by the manufacturer, the saline solution was left at 4° C. for four hours before being used for immunization.

After withdrawing the immunogen required for immumization, a large excess of ice-cold acetone was added to the remaining saline solution, to precipitate out the proteins. The precipitate was rinsed twice with cold acetone and stored in foil, under acetone at 4° C.

Preparation of Mycolic Acids-gelatin Conjugate

A solution of gelatin comprising 5 mg of gelatin in 2 ml of 0.1 N $NaHCO_3$ (pH 8.3) was prepared. An aliquot of 500 $\mu l$ of this solution was added to 600 $\mu l$ of methanol and mixed. This mixture was then added gradually to 2 mg mycolic acids dissolved in 50 $\mu l$ of chloroform over a period of 1 min 20 sec, while vortexing. The sample was then vortexed for a further 30 seconds and placed on ice for 15 minutes.

The sample was transferred to a 100 ml Schott bottle and 80 ml of ice-cold acetone was added. The Schott bottle with its contents was left on ice for 30 minutes. The precipitate comprising mycolic acids adsorbed to gelatin was rinsed twice with acetone and the sample stored under acetone at 40° C.

Immunization of Mice

The immunization of mice was carried out according to the following protocol:

| Duration | Type of manipulation | Site of manipulation |
|---|---|---|
| Day 1 | first immunization | foot pad |
| Day 14 | second immunization | subcutaneous |
| Day 21 | first bleeding | tail vein |
| Day 28 | third immunization | subcutaneous |
| Day 35 | second bleeding | tail vein |
| Day 49 | third immunization | subcutaneous |
| Day 59 | third bleeding | tail vein |

Each of the immunization procedures was accompanied by a control experiment, in which a group of two mice was injected with a carrier molecule and a corresponding adjuvant only, using the same manner of injection.

During the first immunization, five female Balb-C mice were injected in their hind foot cushions with aliquots of the mycolic acids-conjugates and adjuvant mixture. Approximately 50 $\mu l$ of the mixture was injected per foot. During the subsequent immunizations, the same volume of the mixture of mycolic acids conjugates and an adjuvant was introduced subcutaneously.

For the first and subsequent bleedings a few drops of blood was obtained from the tail vein of each mouse, including the control mice.

Monitoring of Antibody Production

Preparation of Sera

For monitoring of the antibody production, a few drops of blood were obtained from the tail vein of each mouse. During the first bleeding, the blood from the five immunized mice and three control mice was pooled and introduced into two separate EPPENDORFF'S (EPPENDORFF is a registered trade mark) tubes, mixed and allowed to clot. The serum was separated from erythrocytes by centrifugation in an Eppendorff's bench centrifuge for 10 min. The collected serum supernatants were stored at 4° C. For the subsequent bleedings, the blood samples were collected and titrated individually.

The ELISA plates were coated with a coating solutions containing either BSA or mycolic acids-gelatin conjugate, at a concentration of 10 $\mu$g/ml in PBS buffer (pH 7.4).

Aliquots of 50 $\mu l$ of the BSA or mycolic acids-gelatin coating solutions were introduced into individual wells and the ELISA plates were incubated for 16 hours at room temperature.

The ELISA plates were then blocked with 200 μl of 0.5% m/v casein in PBS buffer (pH 7.4) per well for one hour at room temperature. The blocking solution was removed by flicking-out and the plates were dried.

Titration of Sera

The sera obtained from the immunized mice were diluted in 0.5% m/v casein in PBS buffer (pH 7.4) and loaded into the ELISA plate in triplicate. Sera originating from control mice, i.e. mice immunized with BSA ADJUPRIME (this is a registered trademark) and from non-immunized mice, were like-wise diluted in 0.5% m/v casein in PBS buffer (pH 7.4) and loaded into the ELISA plate in triplicate, at 50 μl per well.

The direct tritration of sera obtained from mice immunized with BSA-mycolic acid conjugate was accompanied by an inhibition assay, to confirm the specificity of the antibodies. For the inhibition experiments, BSA-mycolic acids conjugate was introduced as a competing antigen at 0.32 mg/ml to the antisera during incubation on the ELISA plate.

The plate was incubated at room temperature for one hour on a plate shaker. After this period, the sera were removed and the plate washed three times with 0.5% m/v casein in PBS buffer (pH 7.4) using an Anthos Autowash.

Goat anti-mouse peroxidase conjugated monoclonal antibodies diluted 1:4000 were introduced into the ELISA plates (50 μl per well) and the plates were left for 60 min at room temperature on a plate shaker. The peroxidase conjugate solution was flicked out and the plates washed three times with the 0.5% m/v casein in PBS buffer (pH 7.4) to remove any excess of the conjugate. The substrate was mixed and pipetted into the wells at 50 μl per well.

The absorbance of the individual wells was followed up for 1.5 hours, using a SLT 340 ATC ELISA reader.

RESULTS AND DISCUSSION OF ELISA IMMUNIZATION EXPERIMENTS

Figure 5:
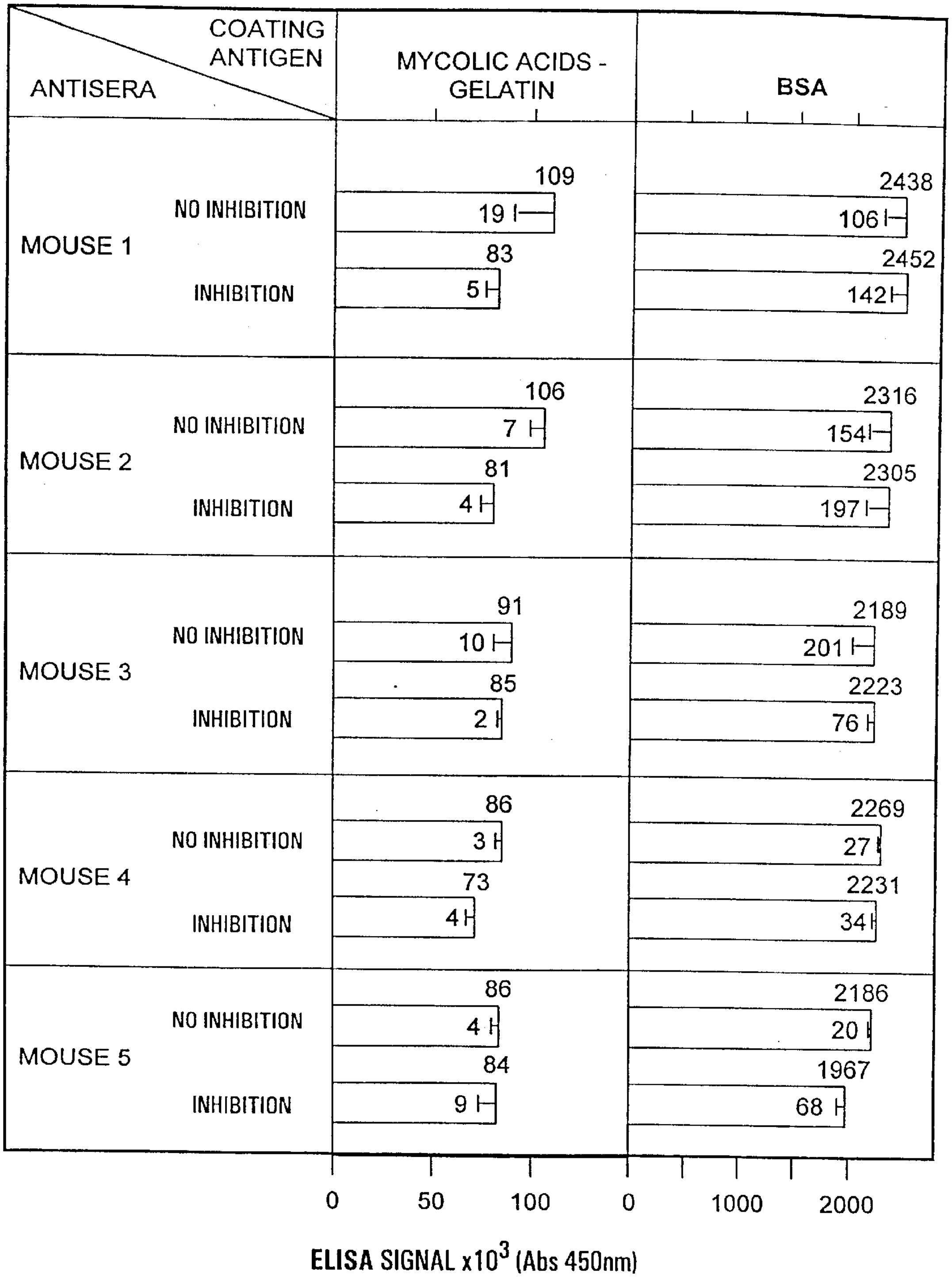
FIG. 5 shows the antibody response obtained by immunizing mice with a mycolic acids-BSA conjugate.

A diagram given in FIG. 5 indicates the antibody response obtained by immunizing mice with the mycolic acids-BSA conjugate. The continuous bars represent the absorbance readings recorded (multiplied by a factor of $10^3$) with the indication of the standard deviation for each set of triplicate dilutions. Strong responses to the BSA carrier (right-hand column) and weaker responses to the mycolic acids (left-hand column) were obtained.

After 59 days into the immunization program two out of five mice immunized produced antisera which exhibited antibody activity with specificity against mycolic acids, as indicated by 24% inhibition of ELISA-signal at 1:50 dilution of antiserum mixed with 0.32 mg/ml soluble BSA-mycolic acids conjugate. The inhibition is effected by blocking the binding sites of mycolic acids-specific antibodies with mycolic acids liganded to BSA in solution, thereby lowering the number of mycolic acids-specific antibodies binding to the ELISA plate.

When BSA was used as coating antigen, strong ELISA-signals were obtained indicating a high degree of immunization of all five mice. No inhibition of the signal of the 1:50 dilution of antiserum obtained from the mice showing anti-mycolic acids activity could be observed by incubating the antisera with 0.32 mg/ml soluble BSA-mycolic acids conjugate. This was probably due to the high concentration of anti-BSA antibodies present, rendering the inhibition of the anti-carrier BSA antibodies out of range of sensitivity.

The anti-mycolic acids immune response requires a more extended immunization period to achieve proper maturation of the response which will lead to an increase in the antibody concentration and/or to increased affinity for the antibodies. Alternatively, the mice can be used for the production of monoclonal antibodies which will be monospecific for mycolic acids.

REFERENCES

Blumberg, L., B. Miller and H. J. Koornhof, 1994. Multiple drug resistant *Mycobacterium tuberculosis*. Tuberculosis—Towards 2000. Book of Abstracts: A scientific conference and workshops on the short-term future of tuberculosis in the developing world, with particular emphasis on Africa, Pretoria, South Africa, 13–17 March 1994, p 9.

Butler, W. R. and J. O. Kilburn, 1988. Identification of Major Slowly Growing Pathogenic Mycobacteria and *Mycobacterium gordonae* by High-Performance Liquid Chromatography of Their Mycolic Acids. *J Clin Microbiol.*, 26, (1), 50–53.

Butler, W. R., K. C. Jost and J. O. Kilburn, 1991. Identification of Mycobacteria by High-Performance Liquid Chromatography. *J Clin Microbiol.*, 29, (11), 2468–2472.

Cantwell, M. C. and N. J. Binkin, 1994. Tuberculosis and HIV in sub-Saharan Africa: Can a good tuberculosis control program make a difference?. Tuberculosis—Towards 2000. Book of Abstracts: A scientific conference and workshops on the short-term future of tuberculosis in the developing world, with particular emphasis on Africa, Pretoria, South Africa, 13–17 March 1994, p 8.

De Cock, K. M., 1994. Impact of Interaction with HIV. In: *Tuberculosis: Back to the Future*, pp 35–52. Edited by J. D. H. Porter and K. Y. P. W. J. Mc Adam. Publishers: John Wiley & Sons, Ltd, Chichester, N.Y., Brisbane, Toronto, Singapore.

Dolin, P. J., M. C. Raviglione and A. Koch, 1994. Global tuberculosis incidence and mortality during 1990–2000. *Bulletin of the World Health Organization*, 72, (2), 213–220.

Godfery-Faussett, P., 1994. Of molecules and men: the detection of tuberculosis, past, present and future. In: *Tuberculosis: Back to the Future*, pp 79–98. Edited by J. D. H. Porter and K. P. W. J. Mc Adam. Publishers: John Wiley & Sons, Ltd, Chichester, N.Y., Brisbane, Toronto, Singapore.

*Laboratory Manual of Tuberculosis Methods*, Tuberculosis Research institute of the SA Medical Research Council (1980, Chapter 6, pp 83–105; Second Edition, revised by E. E. Nel, H. H. Kleeberg and E. M. S. Gatner.

Morse, D. L., 1994. Multidrug resistance—the New York experience. In: *Tuberculosis: Back to the Future*, pp 225–237. Edited by J. D. H. Porter and K. P. W. J. Mc Adam. Publishers: John Wiley & Sons, Ltd, Chichester, N.Y., Brisbane, Toronto, Singapore.

Murray, D. B., 1994. Update on Mycobacterial issues for the Acquired Immune Deficiency Syndrome Era. *J. of Intravenous Nursing*, 17, (4), 217–219.

Musial, C. E., L. S. Tice, L. Stockman and G. D. Roberts, 1988. Identification of Mycobacteria from Culture by using the Gen-Probe Rapid Diagnostic System for *Mycobacterium avium* Complex and *Mycobacterium tuberculosis* Complex. *J Clin Microbiol.*, 26, 2120–2123.

Snider, D. E., 1994. Tuberculosis: the world situation. History of the disease and efforts to combat it. In: *Tuberculosis: Back to the Future*, pp 13–33. Edited by J. D. H. Porter and K. P. W. J. Mc Adam. Publishers: John Wiley & Sons, Ltd, Chichester, N.Y., Brisbane, Toronto, Singapore.

Torres, R. A., S. Mani, J. Altholz and P. W. Brickner, 1990. Human Immunodeficiency Virus Infection Among Homeless Men in a New York City Shelter. *Arch Intern Med.*, 150, 2030–2036.

What is claimed is:

1. A mycobacterial intra-cellular antigen/carrier conjugate wherein the intra-cellular antigen is a purified mycobacterial mycolic acid from *M. tuberculosis* or mixture of purified mycolic acids from *M. tuberculosis* and which is absorbed onto the carrier.

2. A mycobacterial intra-cellular antigen/carrier conjugate according to claim 1, wherein the intra-cellular antigen is a mixture of purified mycolic acids, each purified mycolic acid having the following general structure:

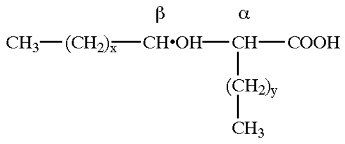

3. A method of raising in a subject an antibody which binds to a mycobacterial mycolic acid or mixture of mycolic acids comprising the step of administering a conjugate according to claim 1 to the subject.

4. A composition comprising a mycobacterial intra-cellular antigen/carrier conjugate according to claim 1 and an adjuvant.

5. A method of raising in a subject an antibody which binds to a mycobacterial mycolic acid or mixture of mycolic acids comprising the step of administering a composition according to claim 4 to the subject.

6. A mycobacterial intra-cellular antigen/carrier conjugate according to claim 1, wherein the carrier is keyhole limpet hemocyanin.

7. A mycobacterial intra-cellular antigen/carrier conjugate according to claim 6, wherein the intra-cellular antigen is a mixture of purified mycolic acids, each purified mycolic acid having the following general structure:

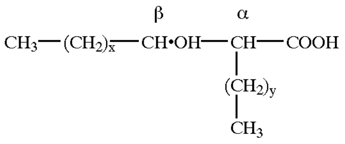

8. A mycobacterial intra-cellular antigen/carrier conjugate according to claim 1 wherein the carrier is a protein.

9. A mycobacterial intra-cellular antigen/carrier conjugate according to claim 8 wherein the protein is gelatin or bovine serum albumin.

10. A mycobacterial intra-cellular antigen/carrier conjugate according to claim 9, wherein the intra-cellular antigen is a mixture of purified mycolic acids, each purified mycolic acid having the following general structure:

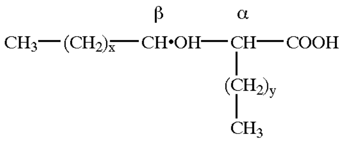

11. A mycobacterial intra-cellular antigen/carrier conjugate according to claim 8, wherein the intra-cellular antigen is a mixture of purified mycolic acids, each purified mycolic acid having the following general structure:

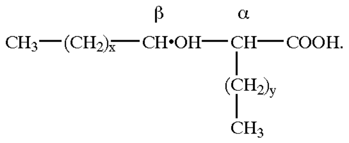

* * * * *